(12) United States Patent
Taylor et al.

(10) Patent No.: US 6,204,230 B1
(45) Date of Patent: *Mar. 20, 2001

(54) ANTIBACTERIAL COMPOSITIONS CONTAINING A SOLVENT, HYDROTROPE, AND SURFACTANT

(75) Inventors: Timothy J. Taylor, Phoenix; Earl P. Seitz, Jr., Scottsdale, both of AZ (US)

(73) Assignee: The Dial Corporation, Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/467,716

(22) Filed: Dec. 21, 1999

Related U.S. Application Data

(63) Continuation-in-part of application No. 09/338,654, filed on Jun. 23, 1999, now Pat. No. 6,107,261.

(51) Int. Cl.[7] ............................. C11D 3/48; C11D 1/83; C11D 3/43

(52) U.S. Cl. ..................... 510/131; 510/130; 510/237; 510/382; 510/386; 510/387; 510/388; 510/432; 510/503; 510/426; 510/427

(58) Field of Search .................. 510/130, 131, 510/237, 382, 386, 387, 388, 432, 503, 426, 427

(56) References Cited

U.S. PATENT DOCUMENTS

| | | | |
|---|---|---|---|
| 743,984 | 1/1956 | Maurice | 81/1 |
| 4,093,745 * | 6/1978 | Wood et al. | 424/358 |
| 4,111,844 * | 9/1978 | Polony et al. | 252/106 |
| 4,350,605 * | 9/1982 | Hughett | 252/305 |
| 4,518,517 * | 5/1985 | Eigen et al. | 252/107 |
| 4,666,615 * | 5/1987 | Disch et al. | 252/11 |
| 4,675,178 * | 6/1987 | Klein et al. | 424/65 |
| 4,702,916 * | 10/1987 | Geria | 424/400 |
| 4,822,602 * | 4/1989 | Sabatelli | 424/65 |
| 4,832,861 * | 5/1989 | Resch | 252/106 |
| 4,851,214 * | 7/1989 | Walters et al. | 424/65 |
| 4,954,281 * | 9/1990 | Resch | 252/107 |
| 4,975,218 * | 12/1990 | Rosser | 252/117 |
| 5,006,529 * | 4/1991 | Resch | 514/721 |
| 5,057,311 * | 10/1991 | Kamegai et al. | 424/70 |
| 5,147,574 * | 9/1992 | Mac Gilp et al. | 252/108 |
| 5,158,699 * | 10/1992 | MacGilp et al. | 252/132 |
| 5,234,618 * | 8/1993 | Kamegai et al. | 252/106 |
| 5,415,810 * | 5/1995 | Lee et al. | 252/545 |
| 5,417,875 * | 5/1995 | Nozaki | 252/106 |
| 5,441,671 * | 8/1995 | Cheney et al. | 252/549 |
| 5,462,736 * | 10/1995 | Rech et al. | 424/401 |
| 5,480,586 * | 1/1996 | Jakubicki et al. | 252/545 |
| 5,635,462 | 6/1997 | Fendler et al. | 510/131 |
| 5,635,468 | 6/1997 | Fowler et al. | 510/406 |
| 5,635,469 * | 6/1997 | Fowler et al. | 510/406 |
| 5,646,100 * | 7/1997 | Haugk et al. | 510/131 |
| 5,653,970 * | 8/1997 | Vermeer | 424/70.24 |
| 5,681,802 * | 10/1997 | MacGilp et al. | 252/132 |
| 5,716,626 * | 2/1998 | Sakurai et al. | 424/401 |
| 5,728,756 | 3/1998 | Gaffar et al. | 524/139 |
| 5,730,963 * | 3/1998 | Hilliard, Jr. et al. | 424/65 |
| 5,824,650 * | 10/1998 | De Lacharriere et al. | 514/15 |
| 5,837,272 * | 11/1998 | Fierro, Jr. et al. | 424/401 |
| 5,851,974 * | 12/1998 | Sandhu | 510/235 |
| 5,863,524 * | 1/1999 | Mason et al. | 424/65 |
| 5,871,718 * | 2/1999 | Lucas et al. | 424/65 |
| 5,888,524 * | 3/1999 | Cole | 424/402 |
| 5,919,438 | 7/1999 | Saint-Leger | 424/70.1 |
| 5,955,408 | 9/1999 | Kaiser et al. | 510/131 |
| 5,985,294 | 11/1999 | Peffly | 424/401 |

FOREIGN PATENT DOCUMENTS

| | | | |
|---|---|---|---|
| 195 30 833 A1 | 2/1996 | (DE) | C11D/1/83 |
| 0 505 935 | 9/1992 | (EP) | C11D/3/48 |
| WO 95/09605 | 4/1995 | (WO) | A61K/7/50 |
| WO 95/32705 | 12/1995 | (WO) | A61K/7/50 |
| 96/06152 | 2/1996 | (WO) . | |
| WO 96/06152 | 2/1996 | (WO) | C11D/3/00 |
| 97/46218 | 12/1997 | (WO) . | |
| WO 97/46218 | 12/1997 | (WO) | A61K/7/48 |
| WO 98/0110 | 1/1998 | (WO) | A61K/7/48 |
| WO 98/55096 | 12/1998 | (WO) | A61K/7/50 |
| WO 98/55097 | 12/1998 | (WO) | A61K/7/50 |

OTHER PUBLICATIONS

PCT International Search Report PCT/US 00/15698 Jun. 07, 2000 ( The Dail Corporation).

Allawala et al., *Journal of the American Pharmaceutical Association*, vol. XLII, No. 5, pp. 267–275 (1953).

Mitchell, *J. Pharm. Pharmacol*, 16, pp. 533–537 (1964).

\* cited by examiner

*Primary Examiner*—Yogendra Gupta
*Assistant Examiner*—Charles Boyer
(74) *Attorney, Agent, or Firm*—Marshall, O'Toole, Gerstein, Murray & Borun

(57) ABSTRACT

Antibacterial compositions having excellent antibacterial effectiveness are disclosed. The antibacterial compositions contain a polyhydric solvent, a hydrotrope, a surfactant, an optional antibacterial agent, and water.

37 Claims, No Drawings

ANTIBACTERIAL COMPOSITIONS CONTAINING A SOLVENT, HYDROTROPE, AND SURFACTANT

CROSS REFERENCE TO RELATED APPLICATIONS

This is a continuation-in-part of U.S. patent application Ser. No. 09/338,654, filed Jun. 23, 1999, now U.S. Pat. No. 6,107,261.

FIELD OF THE INVENTION

The present invention is directed to antibacterial compositions, like personal care compositions, having improved antibacterial effectiveness. More particularly, the present invention is directed to antibacterial compositions comprising a polyhydric solvent, a hydrotrope, a surfactant, and an optional antibacterial agent that provide a substantial reduction, e.g., greater than 99%, in Gram positive and Gram negative bacterial populations within one minute.

BACKGROUND OF THE INVENTION

Antibacterial personal care compositions are known in the art. Especially useful are antibacterial cleansing compositions, which typically are used to cleanse the skin and to destroy bacteria and other microorganisms present on the skin, especially the hands, arms, and face of the user.

Another class of antibacterial personal care compositions is hand sanitizer gels. This class of compositions is used primarily by medical personnel to disinfect the hands and fingers. A hand sanitizer gel is applied to, and rubbed into, the hands and fingers, and the composition is allowed to evaporate from the skin.

Antibacterial compositions in general are used, for example, in the health care industry, food service industry, meat processing industry, and in the private sector by individual consumers. The widespread use of antibacterial compositions indicates the importance consumers place on controlling bacteria and other microorganism populations on skin. It is important, however, that antibacterial compositions provide a substantial and broad spectrum reduction in microorganism populations quickly and without problems associated with toxicity and skin irritation.

In particular, antibacterial cleansing compositions typically contain an active antibacterial agent, a surfactant, and various other ingredients, for example, dyes, fragrances, pH adjusters, thickeners, skin conditioners, and the like, in an aqueous carrier. Several different classes of antibacterial agents have been used in antibacterial cleansing compositions. Examples of traditional antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'-hydroxydiphenylether). Present-day antimicrobial compositions based on such antibacterial agents exhibit a wide range of antibacterial activity, ranging from low to high, depending on the microorganism to be controlled and the particular antibacterial composition.

Most commercial antibacterial compositions, however, generally offer a low to moderate antibacterial activity. Antibacterial activity is assessed against a broad spectrum of microorganisms, including both Gram positive and Gram negative microorganisms. The log reduction, or alternatively the percent reduction, in bacterial populations provided by the antibacterial composition correlates to antibacterial activity. A log reduction of 3–5 is most preferred, a 1–3 reduction is preferred, whereas a log reduction of less than 1 is least preferred, for a particular contact time, generally ranging from 15 seconds to 5 minutes. Thus, a highly preferred antibacterial composition exhibits a 3–5 log reduction against a broad spectrum of microorganisms in a short contact time.

It should be noted that high log reductions have been achieved at pH values of 4 and 9, but such log reductions are attributed at least in part to these relatively extreme pH values. Compositions having such pH values can irritate the skin and other surfaces, and, therefore, typically are avoided. It has been difficult to impossible to achieve a high log reduction using an antibacterial composition having a neutral pH of about 5 to about 8, and especially about 6 to about 8.

For example, WO 98/01110 discloses compositions comprising triclosan, surfactants, solvents, chelating agents, thickeners, buffering agents, and water. WO 98/01110 is directed to reducing skin irritation by employing a reduced amount of surfactant.

Fendler et al. U.S. Pat. No. 5,635,462 discloses compositions comprising PCMX and selected surfactants. The compositions disclosed therein are devoid of anionic surfactants and nonionic surfactants.

WO 97/46218 and WO 96/06152 disclose compositions based on triclosan, organic acids or salts, hydrotropes, and hydric solvents.

EP 0 505 935 discloses compositions containing PCMX in combination with nonionic and anionic surfactants, particularly nonionic block co-polymer surfactants.

WO 95/32705 discloses a mild surfactant combination that can be combined with antibacterial compounds, like triclosan.

WO 95/09605 discloses antibacterial compositions containing anionic surfactants and alkylpolyglycoside surfactants.

WO 98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

N. A. Allawala et al., *J. Amer. Pharm. Assoc.—Sci. Ed., Vol. XLII*, no. 5, pp. 267–275, (1953) discusses the antibacterial activity of active antibacterial agents in combination with surfactants.

A. G. Mitchell, *J. Pharm. Pharmacol., Vol.* 16, pp. 533–537, (1964) discloses compositions containing PCMX and a nonionic surfactant that exhibit antibacterial activity. The compositions disclosed in the Mitchell publication exhibit antibacterial activity in at least 47 minutes contact time, thus the compositions are not highly effective.

Prior disclosures rely upon the presence of a traditional active antibacterial agent (e.g., a phenol compound) in the composition, but have not addressed the issue of which composition ingredient in an antibacterial composition actually provides bacterial control. Prior compositions also have not provided an effective, fast, and broad spectrum control of bacteria at a neutral pH of about 5 to about 8, particularly at pH about 6 to about 8, and especially in the absence of an active antibacterial agent.

An efficacious antibacterial composition has been difficult to achieve because of the properties of the antibacterial agents and the effects of a surfactant on an antibacterial agent. For example, several traditional active antibacterial agents, like phenols, have an exceedingly low solubility in water, e.g., triclosan solubility in water is about 5 to 10 ppm (parts per million). The solubility of the antibacterial agent is increased by adding surfactants to the composition. However, an increase in solubility of the antibacterial agent, and in turn, the amount of antibacterial agent in the composition, does not necessarily lead to an increased antibacterial efficacy.

Without being bound to any particular theory, it is theorized that the addition of a surfactant increases antibacterial agent solubility, but also typically reduces the availability of the antibacterial agent because a surfactant in water forms micelles above the critical micelle concentration of the surfactant. The critical micelle concentration varies from surfactant to surfactant. The formation of micelles is important because micelles have a lipophilic region that attracts and solubilizes the antibacterial agent, which renders the antibacterial agent unavailable to immediately contact bacteria, and thereby control bacteria in short time period (i.e., one minute or less).

The antibacterial agent solubilized in the surfactant micelles will control bacteria, but in relatively long time frames. The antibacterial agent, if free in the aqueous solution and not tied up in the surfactant micelle (i.e., is activated), is attracted to the lipophilic membrane of the bacteria and performs its function quickly. If the antibacterial agent is tied up in the surfactant micelle (i.e., is not activated), the antibacterial agent is only slowly available and cannot perform its function in a time frame that is practical for cleaning the skin.

In addition, antibacterial agent that is solubilized in the micelle is readily washed from the skin during the rinsing process, and is not available to deposit on the skin to provide a residual antibacterial benefit. Rather, the antibacterial agent is washed away and wasted.

Accordingly, a need exists for an antibacterial composition that is highly efficacious against a broad spectrum of Gram positive and Gram negative bacteria in a short time period, and wherein the antibacterial activity is attributed primarily, or solely, to the presence of composition ingredients that are different from a traditional active antibacterial agent. The present invention is directed to such antibacterial compositions.

SUMMARY OF THE INVENTION

The present invention relates to antibacterial compositions that provide a substantial reduction in Gram positive and Gram negative bacteria in less than about one minute. More particularly, the present invention relates to antimicrobial compositions containing a polyhydric solvent, a hydrotrope, a surfactant, water, and an optional active antibacterial agent. In preferred embodiments, the present invention relates to antimicrobial compositions containing a polyhydric solvent, a hydrotrope, a surfactant, water, and an active antibacterial agent, wherein the antibacterial agent is present in an amount of at least 2% of saturation, when measured at room temperature.

Accordingly, one aspect of the present invention is to provide an antibacterial composition comprising:

(a) about 1% to about 50%, by weight, of a polyhydric solvent;

(b) about 1% to about 50%, by weight, of a hydrotrope;

(c) about 1% to about 25%, by weight, of a surfactant;

(d) 0% to about 5%, by weight, of an antimicrobial agent; and (e) water.

Another aspect of the present invention is to provide an effective antibacterial composition that is free of a traditional active antibacterial agent, like a phenol, but includes a polyhydric solvent, hydrotrope, and surfactant, as composition ingredients that effectively and rapidly reduce bacterial populations.

Still another aspect of the present invention is to provide an efficacious antibacterial composition containing a polyhydric alcohol, a hydrotrope, and an anionic surfactant, and that is free of a traditional active antibacterial agent.

Another aspect of the present invention is to provide an antibacterial composition containing a polyhydric solvent, hydrotrope, and surfactant, wherein the weight ratio of hydrotrope to polyhydric solvent is about 1:1 to about 6:1, and preferably about 2:1 to about 4:1, and the surfactant is selected from the group consisting of an anionic surfactant, a cationic surfactant, a nonionic surfactant, an ampholytic surfactant, and mixtures thereof.

Another aspect of the present invention is to provide an antibacterial composition containing a polyhydric solvent, a hydrotrope, a surfactant, and an active antimicrobial agent, wherein active antibacterial agent is present in an amount of at least 2%, and preferably at least 25%, of saturation, when measured at room temperature.

Yet another aspect of the present invention is to provide an antibacterial composition that exhibits a log reduction against Gram positive bacteria (i.e., *S. aureus*) of at least 2 after 30 seconds of contact.

Still another aspect of the present invention is to provide an antibacterial composition that exhibits a log reduction against Gram negative bacteria (i.e., *E. coli*) of at least 2.5 after 30 seconds of contact.

Another aspect of the present invention is to provide an antibacterial composition that exhibits a substantial log reduction against Gram positive and Gram negative bacteria, and has a pH of about 5 to about 8.

Another aspect of the present invention is to provide consumer products based on an antibacterial composition of the present invention, for example, a skin cleanser, a body splash, a surgical scrub, a wound care agent, a hand sanitizer gel, a disinfectant, a mouth wash, a pet shampoo, a hard surface sanitizer, and the like.

A further aspect of the present invention is to provide a method of reducing the Gram positive and/or Gram negative bacteria populations on animal tissue, including human tissue, by contacting the tissue, like the dermis, with a composition of the present invention for a sufficient time, such as about 15 seconds to 5 minutes, to reduce the bacteria level to a desired level. The composition can be wiped or rinsed from the skin, or can be allowed to remain on the skin to allow volatile components of the composition to evaporate.

The above and other novel aspects and advantages of the present invention are illustrated in the following, nonlimiting detailed description of the preferred embodiments.

DETAILED DESCRIPTION OF THE PREFERRED EMBODIMENTS

Personal care products, which typically incorporate a traditional active antibacterial agent, have been known for many years. Since the introduction of antibacterial personal care products, many claims have been made that such products provide antibacterial properties. However, to be most effective, an antibacterial composition should provide a high log reduction against a broad spectrum of organisms in as short a contact time as possible.

As presently formulated, commercial liquid antibacterial soap compositions provide a poor to marginal time kill efficacy, i.e., rate of killing bacteria. Table 1 summarizes the kill efficacy of commercial products, each of which contains about 0.2% to 0.3%, by weight, triclosan (i.e., a traditional antibacterial agent).

TABLE 1

Time Kill Efficacy of Commercial Liquid Hand Soaps

| Product | Organism (Log Reductions after 1 Minute Contact Time) | | |
|---|---|---|---|
|  | Gram Positive S. aureus | Gram negative E. coli | Gram negative K. pneum. |
| Commercial Product A | 1.39 | 0.00 | 0.04 |
| Commercial Product B | 2.20 | 0.00 | 0.01 |
| Commercial Product C | 1.85 | 0.00 | 0.00 |

Present-day products especially lack efficacy against Gram negative bacteria, such as E. coli, which are of particular concern to human health. The present invention, therefore, is directed to antibacterial compositions having an exceptionally high broad spectrum antibacterial efficacy, as measured by a rapid kill of bacteria (i.e., time kill), which is to be distinguished from persistent kill.

The present antibacterial compositions provide excellent time kill efficacy compared to prior compositions. The efficacy of the present compositions is surprising because, unlike prior compositions, the present compositions are free of an active antibacterial agent or contain an active antibacterial agent as an optional ingredient. The antibacterial efficacy of a present invention is related to the presence of a polyhydric solvent, a hydrotrope, and a surfactant. In preferred embodiments, the weight ratio of hydrotrope to polyhydric solvent is about 1:1 to about 6:1. In embodiments wherein an optional active antimicrobial agent is present, the agent is present in an amount of at least 2%, and preferably at least 25%, of saturation, when measured at room temperature.

With respect to "% saturation" of the optional active antimicrobial agent, it has been discovered that the antimicrobial efficacy of an active agent can be correlated to the rate at which the agent has access to an active site on the microbe. The driving force that determines the rate of agent transport to the site of action is the difference in chemical potential between the site at which the agent acts and the external aqueous phase. Alternatively stated, the microbicidal activity of an active agent is proportional to its thermodynamic activity in the external phase. Accordingly, thermodynamic activity, as well as concentration, are important variables with respect to antimicrobial efficacy. As discussed more fully hereafter, thermodynamic activity is conveniently correlated to the percent saturation of the active antibacterial agent in the continuous aqueous phase of the composition.

The % saturation of an active antibacterial agent in any composition, including a surfactant-containing composition, ideally can be expressed as:

$$\% \text{ saturation} = [C/C_s] \times 100\%$$

wherein C is the concentration of antibacterial agent in the composition and $C_s$ is the saturation concentration of the antibacterial agent in the composition at room temperature. The percent saturation, or alternatively the relative thermodynamic activity or relative chemical potential, of an antibacterial active agent dissolved in a surfactant-containing composition is the same everywhere within the composition. Thus, the terms percent saturation of the antibacterial agent "in a composition," "in the aqueous continuous phase of a composition," and "in the micellar pseudophase of a composition" are interchangeable, and are used as such throughout this disclosure.

Maximum antibacterial efficacy is achieved when the difference in thermodynamic activities of the active antibacterial agent between the composition and the target organism is maximized (i.e., when the composition is more "saturated" with the active ingredient). A second factor affecting antibacterial activity is the total amount of available antibacterial agent present in the composition, which can be thought of as the "critical dose." Thus, the two key factors affecting the antibacterial efficacy of an active agent in a composition are: (1) its availability, as dictated by its thermodynamic activity, i.e., percent saturation in the continuous aqueous phase of a composition, and (2) the total amount of available active agent in the solution.

An important ingredient in antibacterial cleansing compositions is a surfactant, which acts as a solubilizer, cleanser, and foaming agent. Surfactants affect the percent saturation of an antibacterial agent in solution, or more importantly, affect the percent saturation of the active agent in the continuous aqueous phase of the composition. This effect can be explained in the case of a sparingly water-soluble antibacterial agent in an aqueous surfactant solution, where the active agent is distributed between the aqueous (i.e., continuous) phase and the micellar pseudophase. For antibacterial agents of exceedingly low solubility in water, such as triclosan, the distribution is shifted strongly toward the micelles (i.e., a vast majority of the triclosan molecules are present in surfactant micelles, as opposed to the aqueous phase).

The ratio of surfactant to antibacterial agent directly determines the amount of active agent present in the surfactant micelles, which in turn affects the percent saturation of the active agent in the continuous aqueous phase. It has been found that as the surfactant:active agent ratio increases, the number of micelles relative to active molecules also increases, with the micelles being proportionately less saturated with active agent as the ratio increases. Since the active agent in the continuous phase is in equilibrium with active agent in the micellar pseudophase, as the saturation of antibacterial agent in the micellar phase decreases, so does the saturation of the antibacterial agent in the continuous phase. The converse is also true. Active agent solubilized in the micellar pseudophase is not immediately available to contact the microorganisms, and it is the percent saturation of active agent in the continuous aqueous phase that determines the antibacterial activity of the composition. The active agent present in the surfactant micelles, however, can serve as a reservoir of active agent to replenish the continuous aqueous phase as the active agent is depleted.

In contrast to prior antibacterial compositions that relied upon traditional active antibacterial agents for efficacy, the present compositions do not rely upon such active antibacterial agents, which are present as optional ingredients. The present compositions rely upon a combination of a polyhydric solvent, hydrotrope, and surfactant, and preferably wherein the hydrotrope and polyhydric solvent are present in a ratio of about 1:1 to about 6:1. If present, the optional antibacterial agent is present in an amount of at least 2% of saturation, when measured at room temperature.

The present compositions are antibacterial compositions having an improved effectiveness against both Gram negative and Gram positive bacteria, and that exhibit a rapid bacteria kill. As illustrated in the following embodiments, an antibacterial composition of the present invention comprises: (a) about 1% to about 50%, by weight, polyhydric solvent; (b) about 1% to about 50%, by weight, of a hydrotrope; (c) about 0.1% to about 25%, by weight, of a surfactant; (d) 0% to about 5%, by weight, of an antibacterial agent; and (e) water. The surfactant preferably is an anionic surfactant. The identity of the surfactant, however, is not limited, especially when the compositions have a weight ratio of hydrotrope to polyhydric solvent of about 1:1 to about 6:1, and preferably about 1.5:1 to about 5:1.

If an active antibacterial agent is present in the composition, the composition has a percent saturation of antibacterial agent in the continuous aqueous phase of at least about 2%, and preferably at least about 25%, when measured at room temperature. The compositions exhibit a log reduction against Gram positive bacteria of about 2 after 30 seconds contact. The compositions exhibit a log reduction against Gram negative bacteria of about 2.5 after 30 seconds contact.

Polyhydric Solvent

A polyhydric solvent is present in the antibacterial compositions in an amount of about 1% to about 50%, and preferably about 5% to about 25%, by weight of the composition. To achieve the full advantage of the present invention, the polyhydric solvent is present in an amount of about 5% to about 15% by weight of the composition.

As defined herein, the term "polyhydric solvent" is a water-soluble organic compound containing two to six, and typically two or three, hydroxyl groups. The term "water-soluble" means that the polyhydric solvent has a water solubility of at least 0.1 g of polyhydric solvent per 100 g of water at 25° C. There is no upper limit to the water solubility of the polyhydric solvent, e.g., the polyhydric solvent and water can be soluble in all proportions.

The term "polyhydric solvent" therefore encompasses water-soluble diols, triols, and polyols. Specific examples of polyhydric solvents include, but are not limited to, ethylene glycol, propylene glycol, glycerol, diethylene glycol, dipropylene glycol, tripropylene glycol, hexylene glycol, 1,3-butylene glycol, 1,4-butylene glycol, 1,2,6-hexanetriol, sorbitol, PEG-4, PEG-6, and similar polyhydroxy compounds.

Hydrotrope

In addition to the polyhydric solvent, an antibacterial composition of the present invention contains a hydrotrope. The hydrotrope is present in an amount up to the solubility of the hydrotrope in water at 25° C., typically in an amount of about 1% to about 50%, and preferably about 5% to about 30%, by weight of the composition. To achieve the full advantage of the present invention, the hydrotrope is present in an amount of about 10% to about 30%, by weight of the composition.

A hydrotrope is a compound that has the ability to enhance the water solubility of other compounds. A hydrotrope lacks surfactant properties, and typically is a short-chain alkyl aryl sulfonate. Specific examples of hydrotropes include, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

In preferred embodiments of the present invention, the weight ratio of hydrotrope to polyhydric solvent is about 1:1 to about 6:1, and preferably about 1.5:1 to about 5:1. To achieve the full advantage of the present invention, the ratio of hydrotrope to polyhydric solvent is about 2:1 to about 4:1. Within this weight ratio of hydrotrope to polyhydric solvent, the identity of the surfactant is not limited. Outside of this weight ratio of hydrotrope to polyhydric solvent, the preferred surfactant is an anionic surfactant.

Surfactant

As stated above, in addition to the polyhydric solvent and hydrotrope, a present antimicrobial composition also contains a surfactant. The surfactant is present in an amount of about 1% to about 25%, and preferably about 2% to about 20%, by weight, of the composition. To achieve the full advantage of the present invention, the antibacterial composition contains about 2% to about 15%, by weight, of the surfactant.

Ready-to-use compositions typically contain about 1% to about 10%, preferably about 1.5% to about 5%, and most preferably, 1.5% to about 3%, of a surfactant, by weight, of the composition. Concentrated compositions suitable for dilution typically contain greater than about 5%, by weight, of a surfactant.

In preferred embodiments, the amount of surfactant is determined such that, if present, the percent saturation of the optional antibacterial agent in the continuous aqueous phase of the composition is at least about 2%, preferably at least about 25%, and most preferably at least about 50%.

The identity of the surfactant is not limited. In particular, when the weight ratio of hydrotrope-to-polyhydric solvent is about 1:1 to about 6:1, the surfactant can be an anionic surfactant, a cationic surfactant, a nonionic surfactant, or a compatible mixture of surfactants. Within this weight ratio, the surfactant also can be an ampholytic or amphoteric surfactant, which have anionic or cationic properties depending upon the pH of the composition. Outside of this ratio, the preferred surfactant is an anionic surfactant.

The antibacterial compositions, therefore, preferably contain an anionic surfactant generally having a hydrophobic moiety, such as a carbon chain including about 8 to about 30 carbon atoms, and particularly about 12 to about 20 carbon atoms, and further has a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference. Numerous other anionic surfactants, and classes of anionic surfactants, are disclosed in Laughlin et al. U.S. Pat. No. 3,929,678, incorporated herein by reference.

Especially preferred anionic surfactants contain no more than two moles of ethoxylation and are selected from the following classes of surfactants: a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ alkoyl sarcosinate, a $C_8$–$C_{18}$ sulfoacetate, a $C_8$–$C_{18}$ sulfosuccinate, a $C_8$–$C_{18}$ alkyl diphenyl oxide disulfonate, a $C_8$–$C_{18}$ alkyl carbonate, a $C_8$–$C_{18}$ alpha-olefin sulfonate, a methyl ester sulfonate, and mixtures thereof. The $C_8$–$C_{18}$ alkyl group contains eight to sixteen carbon atoms, and can be straight chain (e.g., lauryl) or branched (e.g., 2-ethylhexyl). The cation of the anionic surfactant can be an alkali metal (preferably sodium or potassium), ammonium, $C_1$–$C_4$ alkylammonium (mono-, di-, tri), or $C_1$–$C_3$ alkanolammonium (mono-, di-, tri). Lithium and alkaline earth cations (e.g., magnesium) can be used, but antibacterial efficacy is reduced.

Specific preferred anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants. Additional examples of surfactants can be found in "CTFA Cosmetic Ingredient Handbook," J. M. Nikitakis, ed., The Cosmetic, Toiletry and Fragrance Association, Inc., Washington, D.C. (1988) (hereafter CTFA Handbook), pages 10–13, 42–46, and 87–94, incorporated herein by reference.

The antibacterial compositions also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, and mixtures thereof.

Exemplary nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–272; in the CTFA International Cosmetic Ingredient Dictionary, Fourth Ed., Cosmetic, Toiletry and Fragrance Association, Washington, D.C. (1991) (hereinafter the CTFA Dictionary) at pages 1–651; and in the CTFA Handbook, at pages 86–94, each incorporated herein by reference.

In addition to anionic and nonionic surfactants, cationic, ampholytic, and amphoteric surfactants can be used in the antimicrobial compositions. Cationic surfactants include amine oxides and amidoamine oxides, like cocamine oxide, decylamine oxide, and myristyl amine oxide, for example.

Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)-propane-1-sulfonate, sodium 2-(dodecylamino)ethyl sulfate, sodium 2-(dimethylamino) octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

More particularly, one class of ampholytic surfactants include sarcosinates and taurates having the general structural formula

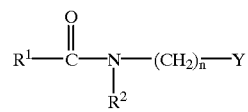

wherein $R^1$ is $C_{11}$ through $C_{21}$ alkyl, $R^2$ is hydrogen or $C_1$–$C_2$ alkyl, Y is $CO_2M$ or $SO_3M$, M is an alkali metal, and n is a number 1 through 3.

Another class of ampholytic surfactants is the amide sulfosuccinates having the structural formula

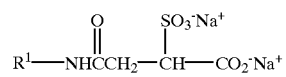

The following classes of ampholytic surfactants also can be used:

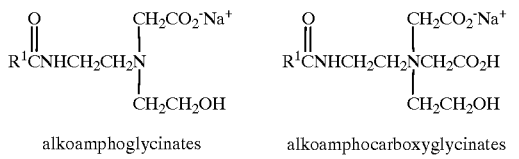

alkoamphoglycinates     alkoamphocarboxyglycinates

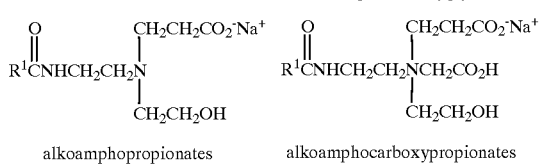

alkoamphopropionates     alkoamphocarboxypropionates

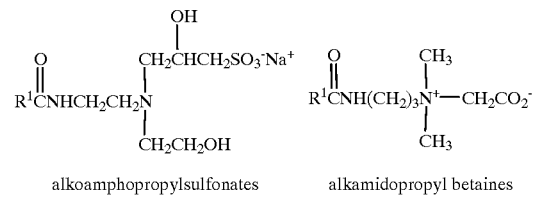

alkoamphopropylsulfonates     alkamidopropyl betaines

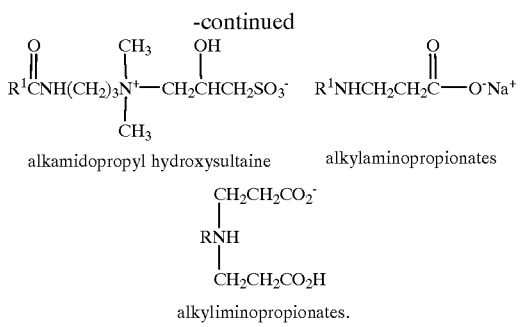

alkamidopropyl hydroxysultaine    alkylaminopropionates alkyliminopropionates.

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Carrier

The carrier of the antibacterial compositions comprises water.

Optional Ingredients

An antibacterial composition of the present invention also can contain optional ingredients well known to persons skilled in the art. For example, the composition can contain an active antibacterial agent or an alcohol. These particular optional ingredients and the amount that can be present in the composition are discussed hereafter.

The compositions also can contain other optional ingredients, such as dyes and fragrances, that are present in a sufficient amount to perform their intended function and do not adversely affect the antibacterial efficacy of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, thickeners, viscosity modifiers, buffering agents, foam stabilizers, antioxidants, skin conditioners and protectants, foam enhancers, chelating agents, gelling agents, opacifiers, vitamins, and similar classes of optional ingredients known to persons skilled in the art.

Specific classes of optional ingredients include alkanolamides as foam boosters and stabilizers; gums and polymers as thickening agents; vitamins A, E, and C as vitamins; inorganic phosphates, sulfates, and carbonates as buffering agents; polyamino acids and salts, like EDTA and phosphates, as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

An alkanolamide to provide composition thickening, foam enhancement, and foam stability can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

Optional Antibacterial Agent

An active antibacterial agent optionally is present in a composition of the present invention in an amount of 0% to about 5%, and preferably about 0.01% to about 3%, by weight of the composition. To achieve the full advantage of the present invention, the antibacterial agent is present in an amount of about 0.01% to about 1%, by weight, of the composition.

The antibacterial compositions can be ready to use compositions, which typically contain 0% to about 2%, preferably 0.01% to about 1.5%, and most preferably about 0.05% to about 1%, of an antibacterial agent, by weight of the composition. The antibacterial compositions also can be formulated as concentrates that are diluted before use with one to about 100 parts water to provide an end use composition. The concentrated compositions typically contain 0% and up to about 10%, by weight, of the antibacterial agent. Applications also are envisioned wherein the end use composition contains greater than 2%, by weight, of the antibacterial agent.

If present at all, a composition of the present invention contains an amount of antibacterial agent that is at least about 2%, and preferably at least about 25%, of the saturation concentration of the antibacterial agent in water, when measured at room temperature. To achieve the full advantage of the present invention, the continuous aqueous phase is about 50% to 100% saturated with the antibacterial agent. The amount of antibacterial agent present in the continuous aqueous phase can be defined as the total amount of antibacterial agent in the composition, less any antibacterial agent present in surfactant micelles. The method of determining percent saturation of antibacterial agent in the composition is disclosed hereafter.

The antimicrobial agents useful in the present invention are phenolic compounds exemplified by the following classes of compounds:

(a) 2-Hydroxydiphenyl compounds

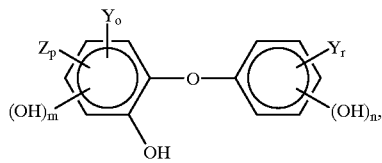

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has the structure:

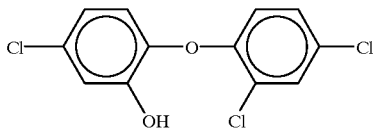

having the adopted name, triclosan, and available commercially under the tradename IRGASAN DP100, from Ciba Specialty Chemicals Corp., Greensboro, N.C. Another useful 2-hydroxydiphenyl compound is 2,2'-dihydroxy-5,5'-dibromodiphenyl ether.

(b) Phenol derivatives

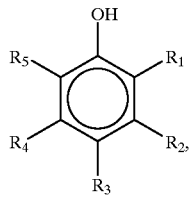

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096, incorporated herein by reference.

(c) Diphenyl Compounds

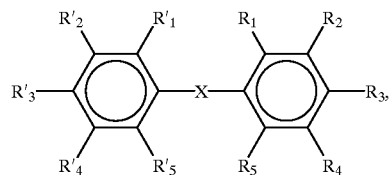

wherein X is sulfur or a methylene group, $R_1$ and $R'_1$ are hydroxy, and $R_2$, $R'_2$, $R_3$, $R'_3$, $R_4R$ , $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3, 3',5,5'-tetrachlorodiphenyl sulfide, 2,2'-dihydroxy-3,5',5,5', 6,6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

Optional Alcohol

Antibacterial compositions of the present invention also optionally can contain 0% to about 20%, by weight, of an alcohol. Preferred embodiments contain 0% to about 15%, by weight, of an alcohol. Most preferred embodiments contain 0% to about 10%, by weight, of a disinfecting alcohol.

As defined herein, the term "alcohol" is a water-soluble alcohol containing one to six carbon atoms. Suitable alcohols include, but are not limited to, methanol, ethanol, propanol, and isopropyl alcohol.

The alcohol can act as a carrier in conjunction with the water. The alcohol also can contribute disinfecting properties to the antibacterial composition.

Optional Gelling Agent

The present antibacterial compositions also can contain 0% to about 5%, by weight, and preferably 0% to about 3%, by weight, of a gelling agent. To achieve the full advantage of the present invention, the antibacterial compositions contain about 0% to about 2.5%, by weight, of a gelling agent. The antibacterial compositions typically contain a sufficient amount of optional gelling agent such that the composition is a viscous liquid, gel, or semisolid that can be easily applied to, and rubbed on, the skin. Persons skilled in the art are aware of the type and amount of gelling agent to include in the composition to provide the desired composition viscosity or consistency.

The term "gelling agent" as used here and hereafter refers to a compound capable of increasing the viscosity of a water-based composition, or capable of converting a water-based composition to a gel or semisolid. The gelling agent, therefore, can be organic in nature, for example, a natural gum or a synthetic polymer, or can be inorganic in nature. Preferred gelling agents are natural or synthetic polymers or derivatives of natural polymers (e.g., polyacrylates, cellulosic gums), like carbomers, polyquaterniums, and carboxymethylcellulosics (e.g., the METHOCEL® products available from Dow Chemical Co., Midland, Mich.).

Optional Skin Conditioners and Protectants

The present antibacterial compositions also can contain optional skin conditioners and/or protectants. Examples of skin conditioners, include emollients, such as, cetyl myristate, glyceryl dioleate, isopropyl myristate, lanolin, methyl laurate, PPG-9 laurate, soy stearyl, octyl palmitate, and PPG-5 lanoate, for example. The skin conditioner also can be a humectant, for example, glucamine and pyridoxine glycol, for example. Occlusive skin conditioners, for example, aluminum lanolate, corn oil, methicone, coconut oil, stearyl stearate, phenyl trimethicone, trimyristin, olive oil, and synthetic wax, also can be used. Combinations of the classes of skin conditioners, in addition to miscellaneous skin conditioners known to persons skilled in the art, alone or in combination can be used. Nonlimiting examples of miscellaneous skin conditioners include aloe, cholesterol, cystine, keratin, lecithin, egg yolk, glycine, PPG-12, retinol, salicylic acid, orotic acid, vegetable oil, and soluble animal collagen. The skin conditioners can be used alone, or in combination with a skin protectant, like petroleum, cocoa butter, calamine, and kaolin, for example. A skin protectant also can be used alone. Additional examples of skin conditioners and protectants can be found in "CTFA Cosmetic Ingredient Handbook," J. M. Nikitakis, ed., The Cosmetic, Toiletry and Fragrance Association, Inc., Washington, D.C. (1988) (hereafter CTFA Handbook), pages 79–85, incorporated herein by reference.

The antibacterial compositions of the present invention do not rely upon a low pH or a high pH to provide a rapid reduction in bacterial populations. Antibacterial compositions of the present invention can have a pH of about 4 to about 9, but at the two extremes of this pH range, the compositions can be irritating to the skin or damaging to other surfaces contacted by the composition. Accordingly, antibacterial compositions of the present invention preferably have a pH of about 5 to about 8, and more preferably about 6 to about 8. To achieve the full advantage of the present invention, the antibacterial compositions have a pH of about 6.5 to about 7.5.

To demonstrate the new and unexpected results provided by the antibacterial compositions of the present invention, the following Examples and Comparative Examples were prepared, and the ability of the compositions to control Gram positive and Gram negative bacteria was determined. The weight percentage listed in each of the following examples represents the actual, or active, weight amount of each ingredient present in the composition. The compositions were prepared by blending the ingredients, as understood by those skilled in the art and as described below.

The following materials were used as ingredients in the examples. The source of each ingredient, and its abbreviation, are summarized below:

a) Alkyl polyglucoside (APG), Henkel Corp., Hoboken, N.J., PLANTAREN 2000N UP (active=55.53%), b) Ammonium lauryl sulfate (ALS), Henkel Corp., STANDAPOL A (active level=28.3%), c) Ammonium xylene sulfonate (AXS), Stepan Corp., STEPANATE AXS (active=40%), d) Cocamidopropyl betaine (CAPB), McIntyre Group, Ltd., Chicago, Ill., MACKAM 35-HP (est. 30% active betaine), e) Dipropylene glycol (DPG), Dow Chemical Co., Midland, Mich., f) Isopropyl alcohol (IPA), g) Monoethanolamine lauryl sulfate (MEALS), Albright & Wilson, Cumbria, England, EMPICOL LQ 33/F (active=33%), h) Octylphenol ethoxylate, 9–10 moles EO (TX100), Union Carbide, TRITON-X 100, i) Potassium cocoate (KCO), McIntyre Group, Ltd., MACKADET 40-K (active=38.4%), j) Potassium laurate (KL), prepared from lauric acid (Sigma, #L-4250, active=99.8%) and potassium hydroxide, k) Potassium oleate (KO), Norman, Fox & Co., Vernon, Calif., NORFOX KO (active=approx. 80%), l) Propylene glycol (PG), Dow Chemical Co., USP Grade (active level=99.96%), m) Sodium cocoamphoacetate (SCA), McIntyre Group, Ltd., MACKAM IC-90 (active=approx. 32%), n) Sodium cumene sulfonate (SCS), Stepan Chemical Co., STEPANATE SCS (active=44.6%), o) Sodium lauryl ether sulfate, 1 mole EO (SLES-1), Henkel, STANDAPOL ES-1 (active=25.40%), p) Sodium lauryl ether sulfate, 2 mole EO (SLES-2), Henkel, STANDAPOL ES-2 (active level=25.71%), q) Sodium lauryl sulfate/sodium dodecyl sulfate (SLS/SDS), BDH Biochemical, BDH Ltd., Poole, England, (active=99.0%), r) Sodium octyl sulfate (SOS), Henkel, STANDAPOL LF (active=32.90%), s) Sodium xylene sulfonate (SXS), Stepan Chemical Co., STEPANATE SXS (active level=40–42%), t) Triclosan (TCS), IRGASAN DP-300, Ciba Specialty Chemicals Corp., Greensboro, N.C. (GC assay on lots used=99.8–99.9% active TCS; mp=56.0–58.0C.), u) Triethanolamine lauryl sulfate (TEALS), Henkel, STANDAPOL T (active=40.1%), v) p-Chloro-m-xylenol (PCMX), NIPACIDE PX-R, Nipa Inc., Wilmington, Del. (about 100% active), and w) Water—distilled or deionized.

The following methods were used in the preparation and testing of the examples:

a) Determination of Rapid Germicidal (Time Kill) Activity of Antibacterial Products. The activity of antibacterial compositions was measured by the time kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. In general, the time kill method is known to those skilled in the art.

The composition can be tested at any concentration from 0–100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about $10^8$ colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

| Organism Name | ATCC # | Abbreviation |
| --- | --- | --- |
| Staphylococcus aureus | 6538 | S. aureus |
| Escherichia coli | 11229 | E. coli |
| Klebsiella pneumoniae | 10031 | K. pneum. |
| Salmonella choleraesuis | 10708 | S. choler. |

S. aureus is a Gram positive bacteria, whereas E. coli, K. pneum, and S. choler. are Gram negative bacteria.

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Tryptone-Histidine-Tween Neutralizer Solution (THT). Decimal dilutions to a countable range then are made. The dilutions can differ for different organisms. Plate selected dilutions in triplicate on TSA+ plates (TSA+ is Trypticase Soy Agar with Lecithin and Polysorbate 80). The plates then are incubated for 25±2 hours, and the colonies are counted for the number of survivors and the calculation of percent or log reduction. The control count (numbers control) is determined by conducting the procedure as described above with the exception that THT is used in place of the test composition. The plate counts are converted to cfu/ml for the numbers control and samples, respectively, by standard microbiological methods.

The log reduction is calculated using the formula

Log reduction=log$_{10}$(numbers control)–log$_{10}$(test sample survivors).

The following table correlates percent reduction in bacteria population to log reduction:

| % Reduction | Log Reduction |
| --- | --- |
| 90 | 1 |
| 99 | 2 |
| 99.9 | 3 |
| 99.99 | 4 |
| 99.999 | 5 | b) Preparation of saturated solutions of TCS in water: A four liter flask was equipped with a 3-inch magnetic stir bar and charged with approximately 7.5 grams (g) TCS and 3 liters (L) of water. The flask then was placed in a water bath, stirred, and heated (40–45° C.) for at least 8 hours. The flask containing the resulting TCS/water suspension was removed from the water bath, and the warm suspension filtered through a Coors #32-H porcelain Buchner funnel equipped with Whatman #40 (5.5cm) filter paper. The filtering assembly was attached to a two liter vacuum filter flask, and filtration was conducted in batches. The filtrate then was transferred to another four liter flask and allowed to cool. Typically, fine needles of TCS crystals formed after the filtrate was stored at room temperature for a few days.

For some time kill studies, the TCS solution was refiltered at room temperature before use in the study. For other time kill studies, a small amount of crystalline TCS was allowed to remain in the test container to ensure saturation in the event of a temperature change. It was assumed that TCS crystals present in the time kill test vessel would not affect test results because crystalline TCS is unavailable to act on the bacteria (i.e., is not solubilized).

To determine the concentration of TCS in the water solutions, filtered samples (in triplicate) were analyzed by HPLC. The apparatus used to filter the solutions was a Whatman AUTOVIAL®, with 0.45 μm PTFE membrane and glass microfiber prefilter, cat. No. AV125UORG. TCS concentrations were calculated using a linear regression line fit (Microsoft EXCEL® software) to TCS/IPA standards included on the same HPLC run.

c) Preparation of aqueous TCS/surfactant compositions: A French square bottle was charged with a solution containing a variable concentration of a surfactant and 0.3%, by weight, TCS. The mixture was stirred and heated (35–40° C.) for several hours until the TCS was solubilized. Variable transformer-controlled heat lamps were used for warming and the temperature of the solution was monitored with a digital thermometer. Stirring then was stopped, TCS seed crystals (about 1 mg) were added to the solution, and the mixture was allowed to stand at about 20° C. In a few days, crystals were observed on the bottom of solution containers in which the maximum solubility of TCS was exceeded.

The approximate concentration of surfactant necessary to almost completely solubilize the 0.3% TCS was determined by use of an experimental design in which the concentration of surfactant was serially reduced by a factor of two over a series of test samples until the approximate saturation point of TCS in the surfactant was observed. Then the difference in concentration (saturated vs. just solubilized) was halved until a close endpoint for TCS saturation could be determined. The saturation point of TCS/surfactant compositions could be effectively estimated with small-scale (15 to 100 mL) samples, but about 600–800 g samples were required to obtain reliable final results. The initial ranges, therefore, were established with small-scale samples, and the final concentrations were determined using larger-scale samples.

d) Preparation of compositions containing TCS, a polyhydric solvent, and a hydrotrope: TCS first was dissolved in the solvent used in the composition. Water then was added to the TCS/solvent composition, followed by the addition of about 1 mg of TCS seed crystals, and the resulting mixture was allowed to stand at about 20° C. to crystallize. In compositions containing a solvent, hydrotrope, and surfactant, the TCS was dissolved in the solvent as above, and then the hydrotrope and surfactant were added to the TCS/solvent solution. The resulting mixture then was diluted to the batch total with water. Adjustment of pH also was performed, if required. The mixture was stirred at room temperature for about an hour, seed TCS was added, and the mixture allowed to stand and crystallize as above. The determination of the TCS saturation point described above also was used (i.e., halving surfactant concentrations). Methods similar to the above for determination of maximum additive concentration have been described in the literature. For example, P. H. Elworthy et al., "Solubilization by surface-active agents and its application in chemistry and biological sciences," Chapman and Hall, Ltd., London, pp. 62–65 (1968), describes determination of concentrations near saturation by observing turbidity of the mixture. A similar technique was used by observing the sample at right angles with a high-intensity light from a small flashlight equipped with a beam focusing attachment (i.e., MINI MAGLITE® AA, MAG Instruments, California, USA).

This method also was used with solutions very near to saturation to enhance observation of small amounts of crystals formed on the bottom of containers.

Table 2 summarizes the results of time kill tests performed on TCS/water compositions. Two series of results, I and II, demonstrate the effect of % saturation in TCS/water compositions, i.e., that within a given test series, reduction in % saturation produces a concomitant reduction in time kill efficacy. Surprisingly, as demonstrated in the following examples, a composition of the present invention provides an effective time kill against Gram positive and Gram negative bacteria, even when an active antibacterial compound is absent from the composition.

TABLE 2

Time Kill Results for Saturated TCS/Water Compositions

| | | TCS (g/mL) | LOG REDUCTION | | | | | | |
|---|---|---|---|---|---|---|---|---|---|
| | | | S. aureus | | E. coli | | K. pneum. | | S. chol. |
| Sample | | (by HPLC) | 1 min/or t | 5 min. | 1 min/or t | 5 min | 1 min/or t | 5 min | 1 min/or t 5 min |
| I | 100% sat'd. | $9.3 \times 10^{-7}$ | 1.07/15s | >3.91 | 0.44/15s | >4.06 | 0.31/15s | >4.00 | |
| | 50% sat'd. | $3.9 \times 10^{-7}$ | 0.03/15s | 1.71 | 0.13/15s | 1.15 | 0.21/15s | 2.76 | |
| | 10% sat'd. | $6.7 \times 10^{-8}$ | 0.03/15s | 0.02 | 0.06/15s | 0.08 | 0/15s | 0.14 | |
| II | 100% sat'd. | $9.6 \times 10^{-6}$ | 3.93 | | 1.76 | | 2.85 | | 2.15 |
| | 50% sat'd. | $4.9 \times 10^{-6}$ | 0.24 | | 0.26 | | 0.35 | | 1.28 |

Comparing the data in Tables 2 and 3 shows that at the very lowest concentration of TCS (i.e., 5 to 10 ppm), the efficacy of time kill is reduced compared to samples containing higher levels of TCS. For example, a sample in Table 2 containing 0.93 ppm TCS has a log reduction of 0.44 after 15 seconds vs. E. coli, whereas a sample in Table 3 containing 484 ppm TCS had a log reduction of 4.13 after 15 seconds vs. the same organism. This effect is more apparent at shorter-contact time periods. Another example, in more complex compositions is illustrated in samples in Table 3, i.e., 50 ppm TCS (est.)/10%PG/5%SXS vs. 448 ppm TCS (est.)/20%PG/10%SXS). The sample with the higher TCS concentration showed at least a log improvement in bacterial reduction after 1 minute.

The data in Table 3 also show differences in efficacy when different solvents/hydrotropes are used with approximately the same TCS concentrations. Table 3 further shows that when the amount of hydrotrope in the composition is less than the amount of polyhydric solvent in the composition, and the composition is free of an antibacterial agent, the composition has a poor time-kill efficacy. Table 3 also shows that if the composition contains only a polyhydric solvent or only a hydrotrope, and is free of an antibacterial agent, that the composition has a poor time-kill efficacy.

TABLE 3

TCS in Solvent and/or Hydrotrope Systems

| TCS | Solvent/ | S. aureus | | E. coli | |
|---|---|---|---|---|---|
| (ppm) | Hydrotrope | sec. | 1 min. | sec. | 1 min. |
| 112 (est) | 17% IPA | | >4.42 | | >3.56 |
| 0 | 17% IPA | | 0.42 | | −0.24 |
| 110 (est) | 23.85% PG | | >4.39 | | 2.37 |
| 342 | 40.01% PG | 4.97[1]/30[2] | >5.17 | 4.29/30 | >4.67 |
| 484 | 41.86% PG | >3.46/15 | >3.46 | 4.13/15 | >4.38 |
| 510 | 42.53% PG | >5.17/30 | >5.17 | 4.47/30 | >4.67 |
| 723 | 44.20% PG | >3.46/15 | >3.46 | >4.38/15 | >4.38 |
| 603 | 45.05% PG | >4.69/15 | >4.69 | 4.21/15 | >4.65 |
| 895 | 47.52% PG | >5.17/30 | >5.17 | 4.42/30 | >4.67 |
| 1385 | 50.00% PG | >4.49/15 | >4.49 | 4.45/15 | >4.65 |
| 0 | 50.00% PG | 0.15/15 | 0.13 | 0.25/15 | 0.26 |
| 0 | 75.00% PG | 1.20/15 | 2.35 | 0.35/15 | 1.73 |
| 63 | 5% SXS | | >4.43 | | 0.96 |
| 0 | 5% SXS | | 0.33 | | −0.15 |
| 57 | 5% SCS | | 3.64 | | 0.80 |
| 0 | 5% SCS | | −0.05 | | −0.11 |
| 448 (est) | 20% PG/10% SXS | >4.14/30 | >4.14 | >5.25/30 | >5.25 |
| 0 | 20% PG/10% SXS | 0.05/30 | 0.05 | 1.16/30 | 1.35 |
| 50 (est) | 10% PG/5% SXS | | 3.42 | | 3.18 |
| 0 | 10% PG/5% SXS | | 0.05 | | 0.35 |
| 50 (est) | 10% PG/5% SCS | | 0.59 | | 4.96 |
| 0 | 10% PG/5% SCS | | −0.03 | | 0.96 |
| 502 (est) | 14.5% DPG/ 10% SXS | >3.63/30 | >3.63 | >4.44/30 | >4.44 |
| 0 | 14.5% DPG/ 10% SXS | 0.03.30 | 0.04 | 0.26/30 | 0.17 |

| TCS | Solvent/ | K. pneum. | | S. chol. | |
|---|---|---|---|---|---|
| (ppm) | Hydrotrope | sec. | 1 min. | sec. | 1 min. |
| 112 (est) | 17% IPA | | >4.11 | | >3.79 |
| 0 | 17% IPA | | 0.89 | | 1.23 |
| 110 (est) | 23.85% PG | | | | |
| 342 | 40.01% PG | 4.33/30 | 5.29 | 2.52/30 | 3.51 |
| 484 | 41.86% PG | 2.96/15 | >3.44 | 1.14/15 | 2.31 |
| 510 | 42.53% PG | 4.61/30 | >5.64 | 1.56/30 | 2.27 |
| 723 | 44.20% PG | >3.44/15 | >3.44 | 1.29/15 | 2.59 |
| 603 | 45.05% PG | 2.60/15 | 4.79 | 1.79/15 | >4.50 |
| 895 | 47.52% PG | 5.26/30 | >5.64 | 2.92/30 | 4.33 |
| 1385 | 50.00% PG | 3.26/15 | >5.04 | 2.69/15 | >4.59 |
| 0 | 50.00% PG | 0.54/15 | 0.63 | 0.17/15 | 0.24 |
| 0 | 75.00% PG | 1.98/15 | >3.44 | 1.34/15 | 3.56 |
| 63 | 5% SXS | | | | |
| 0 | 5% SXS | | | | |

TABLE 3-continued

| TCS in Solvent and/or Hydrotrope Systems | | | | | |
|---|---|---|---|---|---|
| 57 | 5% SCS | | | | |
| 0 | 5% SCS | | | | |
| 448 (est) | 20% PG/10% SXS | >4.32/30 | >4.32 | 3.17/30 | >3.68 |
| 0 | 20% PG/10% SXS | 0.22/30 | 0.37 | 0.25/30 | 1.29 |
| 50 (est) | 10% PG/5% SXS | | | | |
| 0 | 10% PG/5% SXS | | | | |
| 50 (est) | 10% PG/5% SCS | | | | |
| 0 | 10% PG/5% SCS | | | | |
| 502 (est) | 14.5% DPG/ 10% SXS | >4.14/30 | >4.14 | >4.14/30 | >4.14 |
| 0 | 14.5% DPG/ 10% SXS | 0.34/30 | 0.39 | 0.36/30 | 0.47 |

[1]log reduction; and
[2]seconds.

The following examples show the unexpected benefits achieved by compositions of the present invention.

EXAMPLE 1

This example further demonstrates that neither a polyhydric solvent nor a hydrotrope by itself, nor a combination of polyhydric solvent and hydrotrope, provides broad-spectrum, fast-acting, high-efficacy antibacterial activity.

| | | | Log Reduction at 1 minute contact time | | | |
|---|---|---|---|---|---|---|
| Composition No. | Solvent | Hydrotrope | S. aureus | E. coli | K. pneum. | S. chol. |
| 1-1 | 50%[3] PG | 0 | 0.13 | 0.26 | 0.63 | 0.17 |
| 1-2 | 0 | 5% SXS | 0.33 | 0 | — | — |
| 1-3 | 0 | 5% SCS | 0 | 0 | — | — |
| 1-4 | 20% PG | 10% SXS | 0.05 | 1.35 | 0.37 | 1.29 |
| 1-5 | 10% PG | 5% SXS | 0.05 | 0.35 | — | — |
| 1-6 | 10% PG | 5% SXS | 0 | 0.96 | — | — |
| 1-7 | 14.5% DPG | 10% SXS | 0.04 | 0.17 | 0.39 | 0.47 |
| 1-8 | 0 | 7.5% SXS | 0.24 | 0.35 | — | — |
| 1-9 | 0 | 10% SXS | 0.25 | 0.55 | — | — |
| 1-10 | 0 | 12.5% SXS | 0.12 | 0.77 | — | — |
| 1-11 | 0 | 15% SXS | 0.36 | 1.21 | — | — |
| 1-12 | 0 | 17.5% SXS | 0.38 | 1.37 | — | — |
| 1-13 | 0 | 20% SXS | 0.38 | 2.84 | — | — |

[3]% by weight in water

Example 1 clearly shows that a polyhydric solvent alone, even when present at a high concentration of 50%, is not an effective broad-spectrum antibacterial agent. Similarly, the hydrotrope alone, and the combination of polyhydric solvent and hydrotrope, do not provide an effective antibacterial composition.

EXAMPLE 2

This example demonstrates that a surfactant alone, like a polyhydric solvent, hydrotrope, or blend of polyhydric solvent and hydrotrope, does not provide an effective broad-spectrum antibacterial composition.

| Composition | | Log Reduction at 1 minute (time kill) | | | |
|---|---|---|---|---|---|
| No. | Surfactant[3] | S. aureus | E. coli | K. pneum. | S. chol. |
| 2-1 | 0.048% SLS | 0 | 0 | — | — |
| 2-2 | 0.125% SLS | 0.56 | 0.12 | — | — |
| 2-3 | 0.48% SLS | >4 | 0.67 | — | — |
| 2-4 | 1.6% SLS | >3.94 | 1.51 | — | — |
| 2-5 | 1.35% ALS | >3.97 | 0 | — | — |
| 2-6 | 5% SOS | 1.76 | >4.47 | — | — |
| 2-7 | 2.5% KO | 0 | 0 | — | — |
| 2-8 | 3% KL | 0.18 | 1.74 | — | — |
| 2-9 | 4% ALS | >3.61 | 0.24 | 0.15 | 0.04 |

[3]% by weight in water

In this example, sodium lauryl sulfate (SLS), ammonium lauryl sulfate (ALS), and sodium octyl sulfate (SOS) are anionic surfactants, whereas potassium oleate (KO) and potassium laurate (KL) are anionic potassium soaps.

EXAMPLE 3

This example demonstrates that anionic, nonionic, and amphoteric surfactants do not provide fast-acting, broad-spectrum antibacterial compositions, even when the surfactant is combined with a phenolic antibacterial agent (i.e., triclosan or TCS).

| Composition | | | | Log Reduction at 1 minute | |
|---|---|---|---|---|---|
| No. | Surfactant | % Surfactant[3] | TCS[3] | S. aureus | E. coli |
| 3-1 | ALS | 1.35 | 0.3 | >3.17 | 1.39 |
| 3-2 | MEALS | 1.5 | 0.3 | 2.29 | 0.58 |
| 3-3 | TEALS | 1.5 | 0.3 | 2.75 | 1.3 |

-continued

| Composition No. | Surfactant | % Surfactant[3] | TCS[3] | Log Reduction at 1 minute | |
|---|---|---|---|---|---|
| | | | | S. aureus | E. coli |
| 3-4 | KCO | 1.5 | 0.3 | >4.34 | 0.35 |
| 3-5 | KO | 1.0 | 0.3 | 0.55 | 0 |
| 3-6 | KL | 3.0 | 0.3 | 1.06 | 0.82 |
| 3-7 | SLES-1 | 1.25 | 0.3 | >4.39 | 0.41 |
| 3-8 | SLES-2 | 1.0 | 0.3 | >4.25 | 0 |
| 3-9 | TX100 | 4.0 | 0.3 | 0.16 | 0.43 |
| 3-10 | SCA | 1.25 | 0.3 | 0 | 0 |
| 3-11 | CAPB | 1.25 | 0.3 | 0 | 0.21 |
| 3-12 | APG | 2.5 | 0.3 | 0 | 0.01 |

[3]% by weight in water

In this example, SCA and CAPB are amphoteric surfactants. TX100 and APG are nonionic surfactants. MEALS, TEALS, KCO, SLES-1, and SLES-2 are anionic surfactants. Example 3 clearly shows that a wide range of surfactants when formulated with an active antibacterial agent do not provide a fast-acting, broad-spectrum antibacterial composition.

EXAMPLE 4

This example shows that compositions containing a surfactant, a hydrotrope, and a polyhydric solvent provide a surprisingly fast-acting, broad-spectrum antibacterial activity. The following table compares compositions 4-1 through 4-3 to comparative compositions Nos. 1–4 and 2–9.

simply the additive antibacterial properties of 2–9 and 1–4 reveals the antibacterial synergy provided by the ingredients of a composition of the present composition, which is both surprising and unexpected.

Examples 4-2 and 4-3 further illustrate the synergistic properties demonstrated by the present compositions (i.e., Example 4-2) and confirm that the combination of surfactant and solvent (i.e., Example 4-3) is insufficient to account for the antibacterial activity of the present composition.

As illustrated in the following Example 5, the present antibacterial compositions comprise a polyhydric solvent, such as a glycol, like dipropylene glycol, a hydrotrope, like sodium xylene sulfonate, and a surfactant, like ammonium lauryl sulfate. The compositions further optionally can contain an active antibacterial agent, like triclosan, to provide a further antibacterial benefit. As illustrated hereafter, preferred surfactants include anionic surfactants, such as sulfates, sulfonates, and the like. However, with a judiciously selected combination of solvent and hydrotrope, any surfactant can be used in a composition of the present invention. As illustrated hereafter, it surprisingly has been found that a combination of polyhydric solvent, hydrotrope, and surfactant provides a highly effective antibacterial composition demonstrating synergistic activity.

EXAMPLE 5

The following example illustrates compositions of the present invention. This example demonstrates that when a combination of polyhydric solvent, hydrotrope, and surfactant are admixed to form a composition of the present

| | | | | Log Reduction at 1 minute contact time | | | |
|---|---|---|---|---|---|---|---|
| Composition No. | Surfactant[3] | Solvent[3] | Hydrotrope[3] | S. aureus | E. coli | K. pneum. | S. chol. |
| 4-1 | 0.5% ALS | 20% PG | 10% SXS | 3.84 | >4.41 | 1.49 | 2.93 |
| 2-9 | 4% ALS | 0 | 0 | >3.61 | 0.24 | 0.15 | 0.04 |
| 1-4 | 0 | 20% PG | 10% SXS | 0.05 | 1.35 | 0.37 | 1.29 |
| 4-2 | 0.75% ALS | 5% DPG | 15% AXS | 4.24 | >4.5 | 2.57 | 4.68 |
| 4-3 | 0.75% ALS | 5% DPG | 0 | >2.59 | 0.5 | 0.59 | 0.33 |

[3]% by weight in water

Example 1–4 shows that a combination of PG and SXS does not provide an effective antibacterial composition. Overall, Example 1 shows that polyhydric solvents and hydrotropes alone are not effective in providing an antibacterial composition. Example 2–9 further shows that even a high concentration of ALS alone is not effective in providing an antibacterial composition. Example 4-1, however, illustrates the unexpected property of a combination of polyhydric solvent, hydrotrope, and surfactant in providing broad-spectrum, fast-acting antibacterial activity. The observation that the antibacterial effectiveness of Example 4-1 is not invention, the percent saturation of optional, antibacterial agent, e.g., triclosan, in the composition can be low, or zero, and the composition still can demonstrate a high level of antibacterial activity. The polyhydric solvent used in this example is dipropylene glycol, and the surfactant is either sodium lauryl sulfate (noted in the following Table 4 by S) or ammonium lauryl sulfate (noted in Table 4 by A). The hydrotrope is sodium xylene sulfonate. The following Table 4 summarizes the ingredients present in the compositions and Table 5 summarizes the antibacterial activity of these compositions, as measured by time kill.

TABLE 4

| Composition | % TCS[3] | % Saturation of TCS | % Surfactant[3] | % Polyhydric Solvent[3] | % Hydrotrope[3] |
|---|---|---|---|---|---|
| A | 0.30 | 100 | 1.5 (S) | 0 | 0 |
| B | 0.30 | <25 | 10 (S) | 0 | 0 |
| C | 0.30 | 70 | 0.75 (A) | 5 | 15 |

TABLE 4-continued

| Composition | % TCS[3] | % Saturation of TCS | % Surfactant[3] | % Polyhydric Solvent[3] | % Hydrotrope[3] |
|---|---|---|---|---|---|
| D | 0.30 | 35 | 1.5 (A) | 5 | 15 |
| E | 0.30 | 17 | 3.0 (A) | 5 | 15 |
| F | 0.30 | 8 | 6.0 (A) | 5 | 15 |
| G | 0.30 | 4 | 9.0 (A) | 5 | 15 |
| H | 0.30 | 2 | 12.0 (A) | 5 | 15 |
| I | 0.30 | 70 | 0.75 (A) | 5 | 15 |
| J | 0.30 | ~60 | 1.0 (A) | 7.5 | 10 |
| K | 0.30 | ~75 | 0.25 (A) | 14.4 | 10 |
| L | 0.0 | 0 | 0.25 (A) | 14.4 | 10 |
| M | 0.0 | 0 | 0.75 (A) | 5 | 15 |
| N | 0.30 | ~50 | 0.50 (A) | 14.4 | 10 |

[3]% by weight in water

TABLE 5

--Time Kill Results--Log Reductions at 30 seconds/1 minute
("—" indicates the composition was not tested)

| Composition | S. aureus | E. coli | K. pneum. | S. chol. |
|---|---|---|---|---|
| A | —/4.7 | —/0.95 | —/2.5 | —/0.92 |
| B | —/— | —/0.85 | —/0.75 | —/— |
| C | >4.51/>4.51 | >4.63/>4.63 | 4.38/>4.38 | 3.33/>3.88 |
| D | >4.51/>4.51 | >4.63/>4.63 | 3.01/>4.38 | 2.95/>3.88 |
| E | >3.79/>3.79 | >3.93/>3.93 | 2.87/>4.36 | >4.25/>4.25 |
| F | >3.79/>3.79 | >3.93/>3.93 | 2.71/>4.36 | >4.25/>4.25 |
| G | —/— | —/— | >4.04/>4.04 | —/— |
| H | —/— | —/— | 3.74/>4.04 | —/— |
| I | —/— | —/— | 3.49/>3.69 | —/— |
| J | —/— | —/— | 0.17/0.92 | —/— |
| K | >4.59/>4.57 | >4.70/>4.70 | 4.06/>4.41 | >4.04/>4.04 |
| L | 1.7/2.19 | 3.97/>4.70 | 0.50/1.43 | 3.04/>4.04 |
| M | 0.79/0.9 | >4.34/>4.34 | 0.41/1.53 | >4.04/>4.04 |
| N | 4.39/>4.77 | >4.71/>4.71 | 3.00/>4.55 | >4.20/>4.20 |

The compositions of Example 5 demonstrate the surprising and unexpected synergistic antibacterial activity achieved by a combination of solvent, hydrotrope, and surfactant. The antibacterial activity can be further improved by including an optional active antibacterial agent. A surprising aspect of the present composition is that antibacterial activity is demonstrated for compositions in which the saturation of antibacterial agent in the composition is less than about 25% (i.e., compositions E–H), and even zero. In particular, composition H contains TCS in an amount of 2% of saturation.

Compositions A and B demonstrate that, while some antibacterial activity is demonstrated by compositions absent a solvent and hydrotrope, the efficacy of the compositions is limited, even if fully saturated with TCS. Compositions C–H demonstrate that, in the presence of the synergistic solvent/hydrotrope/surfactant combination, high efficacy formulations can be prepared even if the percent saturation of the phenolic antibacterial agent (i.e., triclosan) in the composition is low, i.e., below 25%.

Compositions I and J illustrate the effect of the hydrotrope/polyhydric solvent weight ratio. Composition I has a hydrotrope/solvent ratio of 3/1 and is highly effective against the bacteria K. pneum, whereas composition J has a hydrotrope/solvent ratio of 4/3 and is less effective against the same bacteria. Compositions K, L, and M are alternative embodiments of the present invention. Furthermore, examples L and M show that the present compositions can be formulated without an active antibacterial agent and still have efficacy against a variety of bacteria. Composition N illustrates an effective composition of the present invention that is outside the preferred ratio of hydrotrope to polyhydric solvent.

EXAMPLE 6

The following example illustrates additional compositions of the present invention. This example compares a series of compositions containing a synergistic blend of polyhydric solvent, surfactant, and hydrotrope. Some of the compositions contain triclosan (TCS), and some compositions are free of an active antibacterial agent. The results illustrate the overall antibacterial efficacy of the present compositions.

| Composition | % TCS[3] | % DPG[3] | % SXS[3] | % ALS[3] |
|---|---|---|---|---|
| A | 0.30 | 5 | 15 | 0.75 |
| B | 0.0 | 5 | 15 | 0.75 |
| C | 0.30 | 5 | 15 | 1.5 |
| D | 0.0 | 5 | 15 | 1.5 |
| E | 0.30 | 5 | 15 | 3.0 |
| F | 0.0 | 5 | 15 | 3.0 |

The following table summarizes the time kill results against S. aureus and E. coli for the compositions of Example 6.

| | Log Reductions at 30 seconds and 1 minute | | | |
|---|---|---|---|---|
| | S. aureus | | E. coli | |
| Composition | 30 seconds | 1 minute | 30 seconds | 1 minute |
| A | >4.49 | >4.49 | >4.34 | >4.34 |
| B | 3.25 | 3.88 | >4.34 | >4.34 |
| C | >4.49 | >4.49 | >4.34 | >4.34 |
| D | 3.47 | 4.09 | >4.34 | >4.34 |
| E | >4.49 | >4.49 | >4.34 | >4.34 |
| F | 3.58 | 4.39 | >4.34 | >4.34 |

The data summarized above shows that while all examples A–F exhibit excellent broad-spectrum antibacterial activity, compositions containing TCS (i.e., A, C, and F), exhibited slightly superior antibacterial efficacy and hence are preferred. Thus, the present compositions exhibit excellent antibacterial efficacy in the absence of an active antibacterial agent, and including an active antibacterial agent, (i.e., % saturation is zero) such as TCS, further improves the performance of the present compositions.

EXAMPLE 7

This example illustrates compositions of the invention that can be used as hand cleansers. The compositions of this example include embodiments wherein an antibacterial agent is present in combination with a surfactant, a polyhydric solvent, and a hydrotrope (i.e., Examples 7-A and 7-B). Additionally, Example 7-C is free of a traditional antibacterial agent. The following table summarizes the compositions of Example 7, with the only other ingredient in the compositions being deionized water.

| Composition | % TCS | % DPG | % SXS | % ALS |
|---|---|---|---|---|
| 7-A | 0.30 | 5 | 15 | 1.5 |
| 7-B | 0.30 | 5 | 15 | 3.0 |
| 7-C | 0.0 | 5 | 15 | 3.0 |

The following table contains the results of antibacterial activity of the compositions of Example 7 by the standard time kill method outlined above.

| Composition | % Saturation of TCS | Log Reduction at 30 seconds contact time | |
|---|---|---|---|
| | | S. aureus | E. coli |
| 7-A | 35 | >4.49 | >4.34 |
| 7-B | 17 | >4.49 | >4.34 |
| 7-C | 0 | 3.52 | >4.34 |

Examples 7-A through 7-C each exhibited excellent homogeneity and stability. Examples 7-B and 7-C had superior lather performance in hand wash evaluations using human volunteers. As revealed by the data presented above, even Example 7-C, which is free of the active antibacterial agent triclosan, exhibited a highly effective broad-spectrum antibacterial efficacy. Additionally, Example 7-B, having a percent saturation of TCS significantly less than 25%, exhibited excellent broad-spectrum antibacterial activity. This example illustrates that effective antibacterial compositions having a low percent saturation of TCS can be prepared when it is desirable to emphasize other advantages of compositions having high surfactant concentrations and little to no antibacterial agent.

EXAMPLE 8

This example illustrates the effect of % saturation of TCS in compositions containing a hydric solvent, hydrotrope, and surfactant. From the data summarized in the following table, it is shown that a gain in antibacterial efficacy (as measured by a time kill test) is associated with an increasing % saturation of the antibacterial agent in a given type of composition. The following table shows the effect of varying the concentration of TCS while the concentration of all other components is kept constant.

| Activity Dependence on % Saturation of TCS in Hydric Solvent/Hydrotrope/Surfactant Compositions | | | | |
|---|---|---|---|---|
| | | | Log Reduction (Time Kill) | |
| Triclosan %[3] | Other Ingredients[3] | % Saturation | S. aureus (30 s/60 s) | K. pneum. (30 s/60 s) |
| 0.413 | 5% DPG, 15% SXS, 0.75% ALS | 100 | >4.55/>4.55 | >3.81/>3.81 |
| 0.372 | 5% DPG, 15% SXS, 0.75% ALS | 90 | >4.55/>4.55 | 3.81/>3.81 |
| 0.330 | 5% DPG, 15% SXS, 0.75% ALS | 80 | >4.55/>4.55 | 3.46/>3.81 |
| 0.300 | 5% DPG, 15% SXS, 0.75% ALS | 73 | >4.55/>4.55 | 3.40/>3.81 |
| 0.248 | 5% DPG, 15% SXS, 0.75% ALS | 60 | 3.02/4.05 | 2.73/>3.81 |
| 0.207 | 5% DPG, 15% SXS, 0.75% ALS | 50 | 1.96/3.05 | 2.45/>3.81 |
| 0.166 | 5% DPG, 15% SXS, 0.75% ALS | 40 | 1.94/2.15 | 2.30/>3.81 |
| 0.103 | 5% DPG, 15% SXS, 0.75% ALS | 25 | 1.72/1.93 | 1.34/2.78 |

[3]% by weight in water

The antibacterial compositions of the present invention have several practical end uses, including hand cleansers, mouthwashes, surgical scrubs, body splashes, hand sanitizer gels, and similar personal care products. Additional types of compositions include foamed compositions, such as creams, mousses, and the like, and compositions containing organic and inorganic filler materials, such as emulsions, lotions, creams, pastes, and the like. The compositions further can be used as an antibacterial cleanser for hard surfaces, for example, sinks and countertops in hospitals, food service areas, and meat processing plants. The present antibacterial compositions can be manufactured as dilute ready-to-use compositions, or as concentrates that are diluted prior to use.

The compositions also can be incorporated into a web material to provide an antibacterial wiping article. The wiping article can be used to clean and sanitize skin or inanimate surfaces.

The present antimicrobial compositions provide the advantages of a broad spectrum kill of Gram positive and Gram negative bacteria in short contact times. The short contact time for a substantial log reduction of bacteria is important in view of the typical 15 to 60 second time frame used to cleanse and sanitize the skin and inanimate surfaces.

The present compositions are effective in short contact time because the compositions do not rely upon a traditional active antibacterial agent to reduce microbe populations. The composition, therefore, is available to immediately begin reducing bacterial populations because the antibacterial agent is not present in surfactant micelles. In addition, an antimicrobial agent can be omitted from the composition, and the composition still exhibits excellent antibacterial efficacy.

The following examples illustrate various compositions of the present invention.

EXAMPLE 9

Hand Wash Composition

A composition in accordance with the instant invention, suitable for use as a hand wash, was prepared. The composition contained the following components in their indicated weight percentages:

| Ingredient | Weight Percent |
| --- | --- |
| Triclosan | 0.30 |
| Ammonium Lauryl Sulfate | 0.50 |
| Dipropylene Glycol | 14.4 |
| Sodium Xylene Sulfonate | 10.0 |
| Deionized Water | q.s. |

The composition was prepared by admixing the dipropylene glycol and TCS until homogeneous (about 5 minutes). After the triclosan was completely dissolved, as evidenced by the absence of undissolved solid material, the sodium xylene sulfonate was added to the solution. The resulting mixture then was stirred to completely dissolve the sodium xylene sulfonate. Finally, the ammonium lauryl sulfate and water were added to the resulting solution, and the composition was stirred until homogeneous (about 5 minutes).

The composition had a weight ratio of hydrotrope-to-solvent of about 1:1.44, and was about 50% saturated with triclosan. The composition was evaluated for antibacterial efficacy by a time kill test against S. aureus, E. coli, K. pneum, and S. chol., each at a contact time of 30 seconds. The composition exhibited log reductions against the bacteria of >4.39, >4.71, 3.00, and >4.20, respectively. Thus, the composition exhibited excellent broad spectrum antibacterial activity. This example demonstrates that effective embodiments of the invention can be prepared when the weight ratio of various components is outside the preferred range. However, as exemplified elsewhere herein, preferred embodiments offer additional advantages.

EXAMPLE 10

Body Splash Composition

A composition in accordance with the present invention, suitable for use as a body splash, is prepared using the following ingredients in the following weight percentages:

| Ingredient | Weight Percent |
| --- | --- |
| Triclosan | 0.10 |
| Alkyl Polyglycoside | 1 |
| Propylene Glycol | 5 |
| Sodium Xylene Sulfonate | 15 |
| Fragrance | 0.05 |
| Ethanol | 25 |
| Deionized Water | q.s. |

The composition is prepared by combining the triclosan, propylene glycol, fragrance, and ethanol, and admixing the components until all the triclosan is dissolved, as evidenced by the absence of undissolved material. The sodium xylene sulfonate then is added, and the resulting mixture is stirred until the sodium xylene sulfonate is completely dissolved. Finally, the alkyl polyglycoside and water are added, and the mixture is stirred again until homogeneous. The resulting composition forms a refreshing body splash that provides a desirable level of bacterial reduction on the skin of the user.

EXAMPLE 11

Wet Wipe Composition

A composition in accordance with the present invention, suitable for impregnating into a nonwoven material for the preparation of a wet wipe article, is prepared using the following ingredients in the following weight percentages:

| Ingredient | Weight Percent |
| --- | --- |
| Triclosan | 0.20 |
| Ammonium Lauryl Sulfate | 5 |
| Dipropylene Glycol | 10 |
| Sodium Xylene Sulfonate | 20 |
| Deionized Water | q.s. |

The composition is prepared by admixing dipropylene glycol and TCS until homogeneous (about 5 minutes). After the triclosan is completely dissolved, as evidenced by the absence of undissolved material, the sodium xylene sulfonate is added to the solution. The resulting mixture then is stirred to completely dissolve the sodium xylene sulfonate. Finally, the ammonium lauryl sulfate and water are added to the resulting solution, and the composition is stirred until homogeneous (about 5 minutes).

A piece of nonwoven cellulosic web material (i.e., a commercial paper towel) then is dipped into the composition to form a wet wiper article, suitable for wiping and cleansing surfaces, for example, the hands or an inanimate surface, such as a countertop. The article forms an excellent wet wipe with good detergent properties and provides a broad-spectrum antibacterial activity.

EXAMPLE 12

Hand Wash Composition

A composition in accordance with the present invention, suitable for use as a hand wash, was prepared. The composition contained the following components in their indicated weight percentages:

| Ingredient | Weight Percent |
| --- | --- |
| Triclosan | 0.30 |
| Ammonium Lauryl Sulfate | 6 |
| Dipropylene Glycol | 5 |
| Sodium Xylene Sulfonate | 15 |
| Deionized Water | q.s. |

The composition was prepared by admixing the dipropylene glycol and TCS until homogeneous (about 5 minutes). After the triclosan was completely dissolved, as evidenced by the absence of undissolved material, the sodium xylene sulfonate was added to the solution. The resulting mixture then was stirred to completely dissolve the sodium xylene sulfonate. Finally, the ammonium lauryl sulfate and water were added to the resulting solution, and the composition was stirred until homogeneous (about 5 minutes).

The composition had a weight ratio of hydrotrope-to-solvent of 3:1 and was about 8% saturated with triclosan. The composition was evaluated for antibacterial efficacy by a time kill test against S. aureus, E. coli, K. pneum, and S. chol., each at a contact time of 1 minute. The composition exhibited log reductions against the bacteria of >3.79, >3.93, >4.36, and >4.25, respectively. Thus, the composition exhibited an excellent broad spectrum antibacterial activity. The example demonstrates the advantages of a preferred embodiment of the invention with respect to the weight ratio of hydrotrope-to-solvent, and the inclusion of an active antibacterial agent. Furthermore, this examples demonstrates that effective compositions can be formulated with a higher concentration of surfactant to achieve additional advantages. For example, this composition has improved lather properties and a superior in-use lather stability in hand wash tests using human volunteers.

Obviously, many modifications and variations of the invention as hereinbefore set forth can be made without departing from the spirit and scope thereof, and, therefore, only such limitations should be imposed as are indicated by the appended claims.

What is claimed is:

1. An antibacterial composition comprising:
    (a) about 1% to about 50%, by weight, of a polyhydric solvent;
    (b) about 1% to about 50%, by weight, of a hydrotrope;
    (c) about 1% to about 25%, by weight, of a surfactant;
    (d) 0% to about 5%, by weight, of a phenolic antimicrobial agent; and
    (e) water,
    wherein the weight ratio of hydrotrope-to-polyhydric solvent is about 1:1 to about 6:1, and
    wherein the composition provides a log reduction against Gram positive bacteria of at least 2 after 30 seconds of contact, as measured against *S. aureus*, and a log reduction against Gram negative bacteria of at least 2.5 after 30 seconds of contact, as measured against *E. coli*.

2. The composition of claim 1 wherein the weight ratio of hydrotrope-to-polyhydric solvent is about 1.5:1 to about 5:1.

3. The composition of claim 1 wherein the weight ratio of hydrotrope-to-polyhydric solvent is about 2:1 to about 4:1.

4. The composition of claim 1 wherein the polyhydric solvent is present in an amount of about 5% to about 25%, by weight.

5. The composition of claim 1 wherein the polyhydric solvent is present in an amount of about 5% to about 15%, by weight.

6. The composition of claim 1 wherein the polyhydric solvent comprises a diol, a triol, a polyol, or a mixture thereof.

7. The composition of claim 1 wherein the polyhydric solvent comprises ethylene glycol, propylene glycol, glycerol, diethylene glycol, di-propylene glycol, tripropylene glycol, hexylene glycol, 1,3-butylene glycol, 1,4-butylene glycol, 1,2,6-hexanetriol, sorbitol, PEG-4, PEG-6, or mixtures thereof.

8. The composition of claim 1 wherein the hydrotrope is present in an amount of about 5% to about 30%, by weight.

9. The composition of claim 1 wherein the hydrotrope is present in an amount of about 10% to about 30%, by weight.

10. The composition of claim 1 wherein the hydrotrope is selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof.

11. The composition of claim 1 wherein the surfactant is present in an amount of about 2% to about 20%, by weight.

12. The composition of claim 1 wherein the surfactant is present in an amount of about 2% to about 15%, by weight.

13. The composition of claim 1 wherein the surfactant is selected from the group consisting of an anionic surfactant, a cationic surfactant, a nonionic surfactant, an ampholytic surfactant, and mixtures thereof.

14. The composition of claim 1 wherein the surfactant comprising an anionic surfactant.

15. The composition of claim 1 wherein the anionic surfactant is selected from the group consisting of a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ sulfosuccinate, a $C_8$–$C_{18}$ alkyl diphenyl oxide disulfonate, a $C_8$–$C_{18}$ alkyl carbonate, a $C_8$–$C_{18}$ alphaolefin sulfonate, a methyl ester sulfonate, and mixtures thereof.

16. The composition of claim 1 wherein the phenolic antimicrobial agent is present in an amount of about 0.01% to about 3%.

17. The composition of claim 1 wherein the phenolic antimicrobial agent is present in an amount of about 0.01% to about 1%.

18. The composition of claim 16 wherein the phenolic antimicrobial agent is present in an amount of at least 2% of saturation when measured at room temperature.

19. The composition of claim 16 wherein the phenolic antimicrobial agent is present in an amount of at least 25% of saturation when measured at room temperature.

20. The composition of claim 16 wherein the phenolic antimicrobial agent is present in an amount of at least 50% to 100% of saturation when measured at room temperature.

21. The composition of claim 1 wherein the phenolic antibacterial agent is selected from the group consisting of:

(a) a 2-hydroxydiphenyl compound having the structure

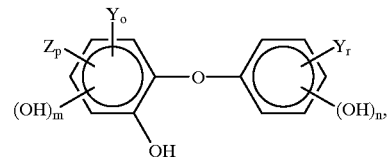

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1;

(b) a phenol derivative having the structure

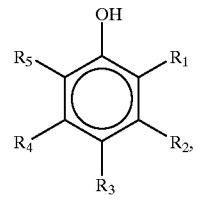

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl, and $R_5$ is hydro or nitro;

(c) a diphenyl compound having the structure

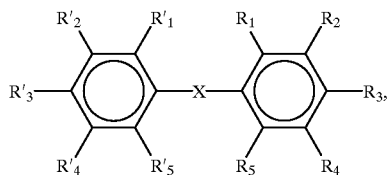

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo; and (d) mixtures thereof.

22. The composition of claim 21 wherein the antibacterial agent comprises triclosan, p-chloro-m-xylenol, or mixtures thereof.

23. The composition of claim 1 further comprising:
0% to about 20%, by weight, of an alcohol, and
0% to about 5%, by weight, of a gelling agent.

24. The composition of claim 23 wherein the alcohol is selected from the group consisting of methanol, ethanol, isopropyl alcohol, n-butanol, n-propyl alcohol, and mixtures thereof.

25. The composition of claim 23 wherein the gelling agent comprises a natural polymer, a synthetic polymer, a derivative of a natural polymer, and mixtures thereof.

26. The composition of claim 1 having a pH of about 5 to about 8.

27. The composition of claim 1 having a pH of about 6 to about 8.

28. The composition of claim 1 comprising:
(a) about 5% to about 15%, by weight, of the polyhydric solvent;
(b) about 2% to about 20%, by weight, of the hydrotrope; and
(c) about 5% to about 20%, by weight, of an anionic surfactant.

29. The composition of claim 28 further comprising about 0.05% to about 1%, by weight, of a phenolic antibacterial agent.

30. The composition of claim 29 wherein the phenolic antibacterial agent is present in an amount of at least 25% of saturation when measured at room temperature.

31. The composition of claim 28 wherein the polyhydric solvent comprises propylene glycol, dipropylene glycol, or a mixture thereof; the hydrotrope comprises a xylene sulfonate; and the surfactant comprises a $C_8$–$C_{18}$ alkyl sulfate.

32. A method of reducing a bacteria population on a surface comprising contacting the surface with a composition of claim 1 for 30 seconds to achieve a log reduction of at least 2 against *S. aureus* and a log reduction of at least 2.5 against *E. coli*.

33. The method of claim 32 further comprising rinsing the composition from the surface.

34. The method of claim 32 wherein the surface is a skin of a mammal.

35. The method of claim 32 wherein the surface is a hard, inanimate surface.

36. The method of claim 32 wherein the composition contacts the surface for 60 seconds to achieve a jog reduction of at least 3 against *S. aureus*.

37. The method of claim 32 wherein the composition contacts the surface for 30 seconds to achieve a log reduction of at least 3.75 against *E. coli*.

* * * * *

UNITED STATES PATENT AND TRADEMARK OFFICE
CERTIFICATE OF CORRECTION

PATENT NO. : 6,204,230 B1
DATED : March 20, 2001
INVENTOR(S) : Taylor et al.

It is certified that error appears in the above-identified patent and that said Letters Patent is hereby corrected as shown below:

<u>Column 34,</u>
Line 29, "jog reduction" should be -- log reduction --

Signed and Sealed this

Nineteenth Day of March, 2002

Attest:

JAMES E. ROGAN
*Director of the United States Patent and Trademark Office*

*Attesting Officer*